Figure 1:
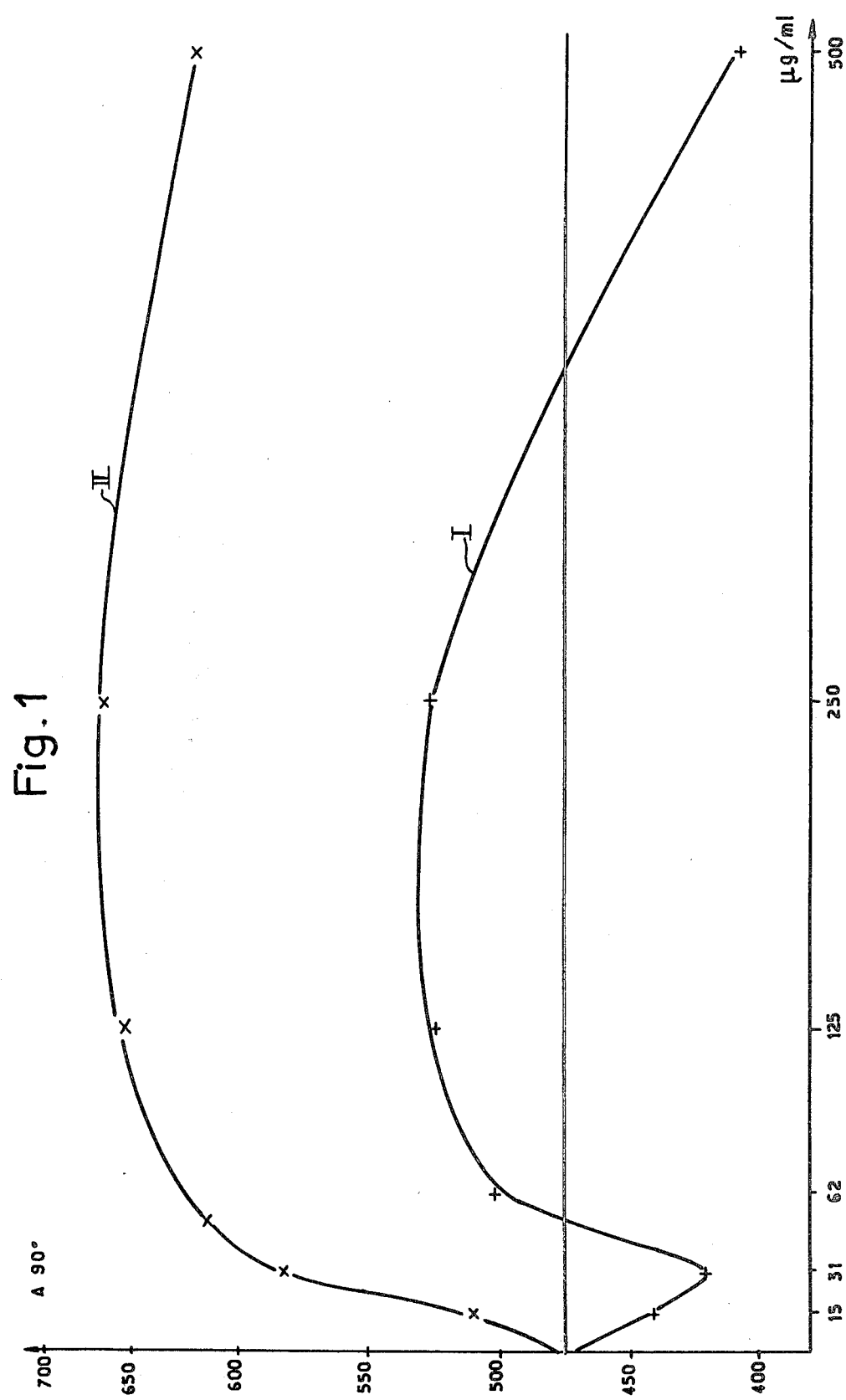

United States Patent [19]

Quash

[11] 4,419,444

[45] Dec. 6, 1983

[54] NOVEL SUPPORTS CARRYING SIDE CHAINS, PROCESSES FOR OBTAINING THESE SUPPORTS, PROCESS FOR ATTACHING ORGANIC COMPOUNDS HAVING CARBOHYDRATE RESIDUES ONE SAID SUPPORTS, PRODUCTS AND REAGENTS RESULTING FROM SAID CHEMICAL FIXATION

[75] Inventor: Gerard A. Quash, Sainte Foy Les Lyon, France

[73] Assignee: Institut National de la Sante et de la Recherche Medicale-INSERM, Paris, France

[21] Appl. No.: 192,479

[22] Filed: Sep. 30, 1980

Related U.S. Application Data

[60] Continuation of Ser. No. 934,003, Aug. 16, 1978, which is a division of Ser. No. 740,840, Nov. 11, 1976.

[30] Foreign Application Priority Data

Nov. 13, 1975 [FR] France ................................ 75 34627
Mar. 26, 1976 [FR] France ................................ 76 08966
Aug. 27, 1976 [FR] France ................................ 76 25898

[51] Int. Cl.³ ..................... G01N 33/50; C12N 11/00; C12N 11/06; C12N 11/08; C12N 11/10; C12N 11/12; C12N 11/14

[52] U.S. Cl. ........................................ 435/7; 435/174; 435/176; 435/178; 435/179; 435/180; 435/181; 435/188; 536/1.1; 260/112 R; 260/121; 436/518; 436/527; 436/529; 436/530; 436/531; 436/532; 436/533

[58] Field of Search ............... 536/1; 435/7, 188, 174, 435/176, 178, 179, 180, 181, 101, 147; 260/112, 121; 436/518, 527, 529, 530, 531, 533, 513, 532, 823

[56] References Cited

U.S. PATENT DOCUMENTS

| | | |
|---|---|---|
| 3,553,310 | 1/1971 | Csizmas et al. ........................... 435/7 |
| 3,947,352 | 3/1976 | Cuatrecasas et al. ............... 435/178 |
| 3,956,113 | 5/1976 | Brenner ................................. 435/178 |
| 3,970,521 | 7/1976 | Zaborsky et al. ................... 435/179 |
| 4,177,038 | 12/1979 | Biebricher ......................... 435/178 |
| 4,217,338 | 8/1980 | Quash ................................. 23/230 B |

OTHER PUBLICATIONS

Lim, et al., "Application of Latex Microspheres in the Isolation of Plasma Membranes", *Biochim. Biophys. Acta*, vol. 394, (1975), pp. 377-387.

Avrameas, et al., "Methods of Fixing Proteins on a Carrier", *Chem. Abstracts*, vol. 72, No. 13, p. 90 (1970) Abs. No. 63566w.

Ray, et al., "Differential Release of Sialic Acid from Normal and Malignant Cells by Vibrio Cholerae Neuramindase or Influenza Virus Neuramindase", *Chem. Abstracts*, vol. 79, No. 8, p. 52 (1973) Abs. No. 49543z.

Grosjean, et al., "Complex Formation between Transfer RNAs with Complementary Anticodons: Use of Matrix Bound tRNA", *Biochem. Biophys. Res. Comm.*, vol. 53, No. 3 (1973) pp. 882-893.

Robberson, et al., "Covalent Coupling of Ribonucleic Acid to Agarose", *Biochem.*, vol. 11, No. 4 (1972), pp. 533-537.

Jakoby et al., *Methods in Enzymology*, vol. 34, (1974), pp. 3-10, 13-30, 72-102.

*Primary Examiner*—Esther M. Kepplinger
*Attorney, Agent, or Firm*—Hubbell, Cohen, Stiefel & Gross

[57] ABSTRACT

Process for chemically binding organic compounds containing carbohydrate residues, onto a support bearing at least one reactive —$NH_2$, in which at least one —$CH_2OH$ group of the carbohydrate residue is transformed in a —CHO group, by oxidation and then the —CHO groups thus obtained are reacted with at least a reactive —$NH_2$ carried by the side chains covalently bound on a solid, insoluble support, the side chains are chosen from among amines, polyamines, diacids, aminoacids, hydrazines, and are eventually coupled, by the intermediary of their reactive —$NH_2$, with a nitrogen-containing compound chosen from aliphatic or aromatic amines, aliphatic or aromatic hydrazines, or amino acids, comprising eventually jointly a —SH group and a —$NH_2$ group.

Products resulting from this process and biological reagents containing said products as their active constituents.

36 Claims, 5 Drawing Figures

675 μg/ml 16 8 4 2 1

NOVEL SUPPORTS CARRYING SIDE CHAINS, PROCESSES FOR OBTAINING THESE SUPPORTS, PROCESS FOR ATTACHING ORGANIC COMPOUNDS HAVING CARBOHYDRATE RESIDUES ONE SAID SUPPORTS, PRODUCTS AND REAGENTS RESULTING FROM SAID CHEMICAL FIXATION

This is a continuation, of application Ser. No. 934,003, filed Aug. 16, 1978, which is a division of application Ser. No. 740,840, filed Nov. 11, 1976.

BACKGROUND OF THE INVENTION

1. Field of the Invention

The present invention relates to novel insoluble solid supports carrying side chains bearing at least a reactive $-NH_2$, to processes for obtaining them, to processes for chemically binding organic compounds having carbohydrate residues on these supports, as well as to the products and to reagents resulting from said chemical fixation.

2. Description of the Prior Art

It is known that biologically active proteins (such as hormones, antigens and enzymes, for example) can be attached to insoluble solid supports comprising latex spheres carrying lateral chains terminating in primary amine functions, by reaction of active groups of the amino acids of the protein chain with the primary amine groups of the support. It has also been proposed to use antigens fixed in the way which has just been very succinctly described above as biological reagents, but in association with developer reagents. The technique which has been mentioned is described notably by R. S. MOLDAY, W. J. DREYER, A. REMBAUM and S. P. S. YEN in "The Journal of Cell Biology", Volume 64 (1975) 75-88 and by R. W. LIM, R. S. MOLDAY, H. V. HUANG and SHIADO-PIN S. YEN in "Biochimica et Biophysica Acta" 394 (1975) 377-387, which relates to the fixation of antibodies on latex spheres by coupling the antibodies through the intermediary of their primary amine functions via covalent bonds onto the latex spheres, which themselves have previously been provided with lateral chains terminating by a primary amine function activated by the action of activators such as glutaraldehyde, cyanogen bromide or watersoluble carbodiimide.

Such a process for coupling proteins through the intermediary of their amino acids always presents a practical difficulty since to carry out the coupling to biologically active amino acids of the protein chain has the effect of reducing, in certain cases, the biological activity of the fixed protein molecule. In addition, the known processes, notably that of R. S. MOLDAY et al give rise to couplings of relatively low stability and of relatively low yields which reduce again their technical and economic interest.

OBJECTS AND SUMMARY OF THE INVENTION

It is consequently an object of the present invention to provide a process for chemically binding biologically active proteins on a support carrying side chains bearing at least a reactive $-NH_2$ without recourse, to effect the coupling, to biologically active groups of the amino acids of the protein chain. In effect, proteins such as antibodies, antigens and a certain number of hormones and enzymes, in particular those the binding of which on supports by chemical coupling has been described in the prior art, are glycoproteins of which the prosthetic groups, namely, carbohydrate residues, do not contribute in any manner to the biological activity of the molecule.

The applicant has now surprisingly developed a process for chemically binding organic compounds having carbohydrate residues, onto a support through the intermediary of said residues, which in addition to not using any active group of the bound organic compound, provide an attachment of very high stability, with satisfactory yields and without diminishing, denaturing or lowering the specific activity of the bound organic compound. The above references to the binding of an "organic compound having carbohydrate residues" are not limited to the binding of glycoproteins: in effect, the process of the invention permits the chemical binding of a given compound through the intermediary of its carbohydrate residue to take place, and the process according to the present invention has a broader scope than the procedures hitherto known in the prior art in that it is applicable not only to glycoproteins but also to other biologically active organic compounds or to those of industrial interest, when they are coupled to a support such as that defined above, provided only that these organic compounds contain carbohydrate residues. Among such "organic compounds containing carbohydrate residues" one can include, inter alia, not only glycoproteins but also polysaccharides and glycolipids.

DESCRIPTION OF THE INVENTION

According to the present invention there is provided a process for chemically binding organic compounds containing carbohydrate residues onto a support bearing at least one reactive $-NH_2$, which process comprises transforming, in a first step, at least one $-CH_2OH$ group of the carbohydrate residue of the organic compound into a $-CHO$ group by oxidation, and, in a second step, reacting the so-obtained $-CHO$ group at least with a reactive $-NH_2$ carried by side chains attached to the insoluble solid support so as to chemically bind the organic compound on said support, and in cases where the reactive $-NH_2$ is a primary amine group, the resulting Schiff base is stabilized, by chemical reduction.

According to one preferred manner of carrying out the process of the invention, the oxidation of the $-CH_2OH$ groups to $-CHO$ groups is effected using sodium periodate.

According to another preferred manner of carrying out the process of the invention, the oxidation of the $-CH_2OH$ groups to $-CHO$ groups is carried out enzymically.

According to another preferred manner of carrying out the process of the invention, an organic compound containing an appropriate carbohydrate residue, prior to the transformation of at least one of the $-CH_2OH$ groups to a $-CHO$ group by oxidation, is subjected to a treatment with neuraminidase, when the terminal residue of the carbohydrate chain is a sialic acid, which treatment eliminates said sialic acid.

Advantageously, where the step of oxidising the $-CH_2OH$ group to a $-CHO$ group is effected enzymically, the enzyme used is selected according to the nature of the last-but-one residue of the carbohydrate chain, from the group comprising the oxidases which oxidise carbohydrates, namely, glucose oxidase, fucose oxidase and galactose oxidase i.e. according to whether the last-but-one residue of the carbohydrate chain is respectively glucose, fucose or galactose.

According to the invention, when the side chain of said support carries a terminal primary amine group, the reaction between the —CHO group of the organic compound to be bound to the support and the said —NH$_2$ group gives rises to a Schiff base, which is stabilised during a third step of the process of the invention, by chemical reduction, using preferably NaBH$_4$.

Such stabilisation is not necessary in the case where the side chains are terminated by a —NH—NH$_2$ group, which forms a stable hydrazone in the presence of —CHO groups; in cases where the side chain carried both as —NH$_2$ and a —SH, their interaction with a —CHO group also gives rise to the formation of a stable heterocyclic compound, which, for instance, can be a thiazolidine in the case of cystein, where the —SH is in a β-position with respect to the —NH$_2$.

The process according to the present invention for chemically binding compounds containing carbohydrate residues onto solid, insoluble supports having side chains with at least a reactive —NH$_2$, can give rise to coupled products which are useful, in particular as biological reagents.

The applicant has established that, surprisingly, the reactivity and stability of the coupled products so obtained are greatly increased if the length of the side chain is itself sufficiently increased. It has also been established that, surprisingly, diagnostic reagents comprising the aforementioned coupled products possess qualities of sensitivity and precision which are not possessed by diagnostic reagents of similar type proposed in the prior art.

The supports used for the chemical binding of the organic compounds having at least one —CHO group, are insoluble, solid supports selected notably from the group which comprises latex spheres, agarose or dextrane beads, activated glass beads or the like, on which are covalently bound side-chains bearing at least a reactive —NH$_2$ resulting from the binding onto the said supports, of compounds selected among the amines, polyamines, diacids, amino-acids, aliphatic or aromatic hydrazines bearing eventually an acid group.

Among these supports, those which are new and are within the scope of the present invention, are supports on which are covalently bound side-chains bearing at least a reactive —NH$_2$ resulting from the binding on said supports, of a compound selected among the aromatic amines, polyamines other than diamines, substituted amino-acids, aliphatic or aromatic hydrazines bearing eventually an acid group.

According to a particularly advantageous embodiment of the invention, the side-chains bound to the supports, be they known supports or the new ones according to the present invention, are coupled through the intermediary of their reactive —NH$_2$, with a nitrogeneous compound also containing at least a reactive —NH$_2$ and chosen notably among the aliphatic or aromatic amines and/or aliphatic or aromatic hydrazines, or amino-acids, notably those containing both an —NH$_2$ and a —SH capable of forming an heterocycle in the presence of the —CHO group of the organic compound to be bound.

Advantageously, the insoluble solid supports on which are bound the aforementioned side chains carry carboxyl groups through which the side chains are bound to said supports.

In another preferred embodiment of supports according to the invention, the insoluble solid supports carry —NH$_2$ groups through which the abovementioned side chains are bound to the support.

According to the invention, the amines or polyamines bound to the solid insoluble supports are selected from aromatic diamines, polyamines other than aliphatic diamines, and substituted amino-acids.

Advantageously, there are bound to the abovementioned supports: aromatic diamines, polyamines containing primary and secondary amine groups having, for example, the following formula:

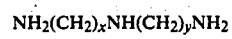

where $x \geq 3$ and $y \geq 3$
and having the formula:

where $x \geq 3$, $y \geq 4$ and $z \geq 3$,
or appropriate substituted amino-acids, among which can be included compounds containing a —SH group as in cystein of the formula:

According to an advantageous embodiment of the invention, the side chains bound to the support result from coupling an aliphatic or aromatic amine, such as a diamine, polyamine or amino-acid, with other aliphatic or aromatic amines such as, in particular: diamines, polyamines, aliphatic or aromatic hydrazines or their derivatives.

According to a particularly advantageous embodiment of the invention, the solid insoluble support carries hexamethylenediamine (HMD) chains advantageously coupled through the intermediary of their reactive —NH$_2$, to adipic dihydrazide, to p-hydrazino-benzoic acid, or the like.

According to a further particularly advantageous embodiment of the invention, the insoluble solid support carries polyamine chains, such as spermidine, diaminopropylamine and spermine, for example, advantageously coupled through the intermediary of their reactive —NH$_2$, to adipic dihydrazide, to p-hydrazinobenzoic acid or the like.

According to a further advantageous embodiment of the present invention, the insoluble solid supports carry side chains comprising an amino-acid such as β-alanine or ε-aminocaproic acid, for example, advantageously coupled to diaminopropane, to adipic dihydrazide, to p-hydrazino-benzoic acid or to analogous compounds.

According to another advantageous embodiment of the invention, the insoluble solid supports carry side chains ending with an amino-acid carrying a —SH group, as for example cysteine.

According to an advantageous provision of said embodiment, the amino-acid carrying a —SH group is coupled to an aliphatic or aromatic diamine.

The present invention also provides a process for binding side chains having a reactive —NH$_2$ onto an insoluble solid support selected notably from latex spheres, dextrane or agarose beads, beads of activated glass and the like, which comprises binding the aforementioned side chains onto the support in the presence of an appropriate condensation agent, the fixation process including eventually a subsequent coupling step of said chains with nitrogen-containing compounds advantageously selected, in particular, among amines, aliphatic or aromatic hydrazines, amino-acids, which coupling step is also advantageously effected in the presence of an appropriate coupling agent, such as carbodiimide or N-hydroxy-succinimide.

According to the invention, one advantageously uses as the condensation and/or coupling agent glutaraldehyde or a totally or partially water-soluble carbodiimide of the general formula:

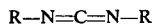

in which R represents notably an alkyl radical having 2 to 12 carbon atoms, and particularly an ethyl, n-propyl, isopropyl, n-butyl, sec-butyl, tert-butyl, isobutyl, amyl, hexyl, heptyl, octyl, nonyl, decyl, undecyl, dodecyl; a cycloalkyl radical having 5 or 6 carbon atoms; a monoaryl substituted lower alkyl radical such as, for example, a benzyl or $\alpha$- or $\beta$-phenylethyl radical; a monoaryl radical such as, for example, a phenyl, morpholino- or piperidyl radical; a lower alkoyl radical substituted by a morpholinyl group, such as, for example, an ethylmorpholinyl radical; a lower alkyl radical substituted by a piperidyl group, such as, for example, an ethylpiperidyl radical; a lower dialkylamino radical; a lower alkyl radical substituted by a pyridyl group, such as, for example, an $\alpha$-, $\beta$-, or $\gamma$-methyl- or ethyl-pyridyl radical; their acid addition salts with acids and their quaternary ammonium salts, the two R radicals being identical or different.

According to a preferred embodiment of the process of the invention, the covalent binding of the side chains on the support is effected in a non-agglutinant buffer, containing no free —$NH_2$ groups and at a pH between 6,0 and 8,8.

According to another preferred embodiment of the process of the invention, the covalent binding is followed by dialysis against the same buffer as that used for the binding.

The solid insoluble supports having side chains obtained according to the present invention are themselves novel products, which are capable of numerous industrial applications.

One of these applications consists in using them as supports for organic compounds having at least one —CHO group, chemically bound on said supports by reaction between their —CHO group and the reactive —$NH_2$ of the side chains of said supports.

This application presents a particular interest in the case of the binding of organic compounds comprising carbohydrate residues, which is effected through the intermediary of said carbohydrate residues, in modifying initially by oxidising two adjacent functional groups carried by the latter into —CHO groups, then bringing these —CHO functions to react at least with a reactive —$NH_2$ of the side chains to the solid insoluble support.

The oxidation of the carbohydrate residues of the organic compound to be bound to the support is preferably effected at about pH 6.

Advantageously, the excess oxidising agent is eliminated at the end of the abovementioned oxidation reaction, by all appropriate means, such as dialysis or addition of an agent capable of being oxidized by the oxidizing agent, such as sodium sulfite, glycerol, glucose and the like.

The interest of the above application is increased when the organic compounds having carbohydrate residues at least partially oxidised to a —CHO, bound to the supports according to the present invention, are selected from glycoproteins, polysaccharides and glycolipids; in effect, antigens, antibodies a certain number of enzymes and hormones belonging to the group of glycoproteins and their fixation to an insoluble solid support through the intermediary of their carbohydrate residues which have previously been oxidised to an aldehyde, allows their free protein moiety or their free lipidic moiety (for glycolipids) to be utilised in carrying out tests allowing the precise detection, with high sensitivity, which can be of the order of nanograms of detectable antigen, using the insoluble diagnostic agents realised in this way.

According to the present invention, one again improves the ease of using biological reagents which make them also form further aspects of the present invention, by chemically binding glycoproteins, glycolipids or polysaccharides with solid insoluble supports carrying side chains bearing a reactive —$NH_2$, selected from basic dyes.

One thus obtains coloured biological reagents which allow immunological reactions to be revealed (with antigens or their antibodies in particular) by direct reaction, notably agglutination reactions without having hereafter to resort to the intermediary of red corpuscles, the reading of the results of agglutination reactions in thus found to be greatly facilitated.

According to the invention, these solid, insoluble coloured supports are prepared by binding side chains on the supports in an appropriate buffer, in the presence of a coupling and/or condensation agent added in two successive steps, and selected from, notably, glutarladehyde, N-hydroxy-succinimide and totally or partially water-soluble carbodiimides, the binding process being followed by desorption of remaining non-coupled reagents.

According to an advantageous method of preparing the coloured supports, these are maintained, before use, in a nonagglutinating buffer.

Numerous biological reagents can be prepared and put to use in accordance with the present invention, these ragents distinguishing themselves by their excellent stability and their high sensitivity.

The coupled products resulting from the chemical binding of organic compounds having carbohydrate residues on a solid insoluble support having side chains bearing at least a reactive —$NH_2$ according to the present invention, can also be used as catalysts in numerous chemical, biochemical and biological reactions.

Having regard to the foregoing, the invention includes many alternative embodiments which will be apparent from the following description.

The invention has for its aim more particularly the processes of chemical binding of organic compounds containing carbohydrate residues, on a support having at least one reactive —$NH_2$, according to the foregoing description, to the products thereof, to reagents and catalysts comprising the coupled products obtained in putting these processes into operation and the means themselves of putting into operation these processes and obtaining the said products, reagents and catalysts.

The invention will be better understood with the aid of the supplementary description which follows, which refers to examples of supports and novel products according to the invention, as well as to examples of the preparation of diagnostic reagents according to the present invention, of which the high sensitivity and precision are shown in the frame-work of tests by radioactivity and nephelometry.

It must be well understood, however, that these examples are given solely for the purpose of illustrating the objects of the invention, of which they do not constitute in any manner a limitation.

EXAMPLES

I.—EXAMPLES OF PREPARATION OF SOLID INSOLUBLE SUPPORTS ACCORDING TO THE PRESENT INVENTION

A. EXAMPLES OF PREPARATION OF SOLID INSOLUBLE SUPPORTS CARRYING SIDE CHAINS ABLE TO BE COUPLED TO ANOTHER NITROGEN-CONTAINING COMPOUND CARRYING A REACTIVE —NH$_2$

A$_1$—PREPARATION OF SUPPORTS FROM CALIBRATED SPHERICAL PARTICLES OF CARBOXYLATED POLYSTYRENE BEARING SIDE CHAINS CARRYING AT LEAST A REACTIVE —NH$_2$

EXAMPLE 1

PREPARATION OF A SUPPORT CARRYING HEXAMETHYLENEDIAMINE SIDE CHAINS

To 12 mg of "ESTAPOR PSI$_{68}$" (Rhone-Progil Registered Trade Mark designating calibrated spherical particals of carboxylated polystyrene of diameter of the order of 0.22μ) bearing free —COOH groups in suspension in a borate buffer of composition 0.14 M NaCl, 0.01 M Borate-HCl of pH 8.1 (BBS) were added 80 μmoles of hexamethylene-diamine (HMD). The mixture was shaken at 20° C. for three hours in the presence of 0.02 M of 1-ethyl 3-(3-dimethylaminopropyl-carbodiimide)-chlorhydrate (EDC). Thereafter, the suspension was dialysed against BBS buffer until its O.D. at 230 nm was equal to zero.

One obtained a support of "Estapor" carboxylated hexamethylenediamine ("Estapor"-HMD).

EXAMPLE 2

PREPARATION OF A SUPPORT BEARING SIDE CHAINS CONSTITUTED BY POLYAMINE

The procedure described in Example 1 was followed, except that spermine was used in place of HMD.

EXAMPLE 3

FIXATION OF A SIDE CHAIN CONSTITUTED BY AN AMINO ACID ON AN INSOLUBLE SUPPORT

To 20 mg of "Estapor PSI$_{42}$" carrying free —COOH groups in suspension in a BBS buffer of pH 8.5 were added 20 μmoles of ε-amino-caproic acid of which the primary amino group is not in the alpha position. The mixture was shaken for three hours at about 20° C. in the presence of 0.02 M of EDC. Thereafter, the suspension was dialysed against BBS buffer until the O.D. at 230 nm was equal to zero. The fixation of the amino acid on the support was effected through the intermediary of the CONH(CH$_2$)$_5$COOH groups which formed at the level of the free —COOH groups of the support.

EXAMPLE 4

FIXATION OF CRESYL VIOLET

To 10 mg of "Estapor" (registered trade mark of Rhone-Progil to designate carboxylated polystyrene) having free —COOH groups in suspension in 5 ml of 0.14 M NaCl-0.01 M Borate-HCl of pH 8.1 (BBS), is added a solution of Cresyl violet obtained by filtration on a 0.22μ "Millipore" of a suspension of 20 mg of ultrasonically-treated Cresyl violet. The mixture was shaken for 12 hours at 20° C. in the presence of 0.05 M of 1 ethyl-3(3-dimethylaminopropylcarbodiimide)hydrochloride (EDC). At the end of this period, one renewed the addition of EDC and continued the shaking for 12 hours.

Thereafter, the suspension was centrifuged at 20,000 g for 1 hour and the residue taken up in 0.1 M acetone buffer of pH 5.5 and recentrifuged to eliminate the excess Cresyl violet. This operation was repeated until the supernatant was clear. One then eliminated the acetate by forming a hydrochloride by three successive washings with 0.1 N HCl, followed by two washings with 0.1 N NaOH, in order to regenerate the amine functions, then two washings in BBS of pH 8.8 to eliminate the excess NaOH.

The obtained product was maintained in a 0.1 M phosphate buffer of pH 7.

EXAMPLE 5

FIXATION OF BASIC FUCHSINE

One proceeded in the manner described in EXAMPLE 4, but in place of the 20 mg of Cresyl violet, one added 2 ml of a saturated solution of basic fuchsine.

EXAMPLE 6

PREPARATION OF SUPPORTS FROM DOW 816 CARBOXYLATED POLYSTYRENE

The coupling reactions described above on "Estapor" carboxylated polystyrenes obtained from Rhone-Poulenc and on glass beads have equally been carried out on Dow 816 carboxylated polystyrene spheres obtained from Dow Chemical Corporation, in proceeding to adapt the method of carrying out the coupling reactions of the side chains on the aforementioned spheres, one takes account of a number of available —COOH groups on the spheres with regard to those on the "Estapor" spheres.

To 180 mg of Dow 816 particles were added 560 mg of hexamethylenediamine (HMD) in 20 ml (final) of 0.14 M NaCl, 0.01 M borate-HCL of pH 8.1. Some 1-ethyl3-3-dimethylaminopropyl)carbodiimide (EDC) was added to a final concentration of 0.5 M in two successive additions. After shaking at 4° C. for 8 hours, the Dow spheres were washed by three successive centrifugations at 20,000 g for 30 minutes with the same buffer and finally suspended in 13 ml of 0.1 M phosphate buffer of pH 6.

A₂—PREPARATION OF SUPPORTS FROM GLASS BEADS BEARING SIDE CHAINS CARRYING A REACTIVE —NH₂

EXAMPLE 7

FIXATION OF HMD SIDE CHAINS ON GLASS BEADS

To 1 g of glass beads bearing free —COOH groups (sold under the commercial designation "CPG/carboxyl" by Corning Glass Works (dimension of pores: 550 A; diameter: 177–840 microns), were added 5 ml of 0.1 M phosphate buffer of pH 7.0 and the suspension was degassed under vacuum. 50 μmoles of HMD were added in solution in the same buffer and the mixture was shaken gently at 4° C. for 18 hours in the presence of 0.5 M of EDC. Thereafter, the glass beads were washed with phosphate buffer.

The terminal —NH₂ groups of the HMD side chains fixed to the glass beads were coupled to a hydrazine in the manner described in EXAMPLE 13 in the case of an aliphatic hydrazine or in the manner described in EXAMPLE 11 in the case of an aromatic hydrazine.

EXAMPLE 8

BINDING OF A POLYAMINE ON A SIDE CHAIN TERMINATED BY AN N-HYDROYL-SUCCINIMIDE GROUP CARRIED BY GLASS BEADS 2 g of commercially available glass beads known under the designation "CPG/N-OH succinimide" (sold by Corning Glass Works) and represented by the formula:

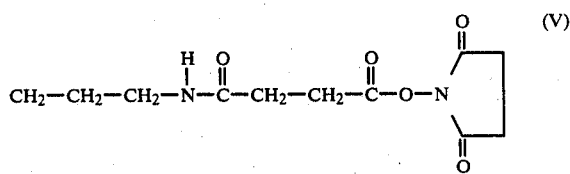

were suspended in 10 ml of BBS buffer at pH 8.2 and degassed under vacuum and 40μ moles of spermine added thereto. The mixture was shaken gently for 16 hours at 4° C., then washed with BBS buffer to eliminate the reaction products.

The —NH₂ terminals of polyamine residues were themselves coupled to aliphatic or aromatic hydrazines according to the technique described in EXAMPLES 11 and 13.

A₃—PREPARATION OF SUPPORTS FROM AGAROSE GEL BEADS BEARING SIDE CHAINS CARRYING A REACTIVE —NH₂

EXAMPLE 9

BEADS OF AGAROSE GEL CARRYING SIDE CHAINS OF ε-AMINO-CAPROIC ACID

"CH-SEPHAROSE" (registered trade mark of Pharmacia, Upsala, Sweden to designate beads of agarose gel) already carry side chains of ε-amino-caproic acid.

B—EXAMPLES OF PREPARATION OF SOLID INSOLUBLE SUPPORTS CARRYING SIDE CHAINS ABLE TO REACT WITH THE —CHO GROUPS OF THE COMPOUNDS TO BE BOUND ONTO SAID SUPPORTS

B₁—BINDING OF TERMINAL FUNCTIONAL GROUPS CONSTITUTED BY HYDRAZINES

B₁.₁—CONSTITUTED BY AROMATIC HYDRAZINES

EXAMPLE 10

PREPARATION OF AN "ESTAPOR"-HMD-P-HYDRAZINOBENZOATE SUPPORT 4 mg of "Estapor"-HMD of 0.22μ diameter were suspended in 2 ml of borate buffer comprising 0.14 M NaCl, 0.01 M borate-HCl, of pH 8.8. To this suspension were added 22μ moles of hydrazinobenzoic acid dissolved in BBS. The volume was adjusted to 4 ml with BBS. After the addition of 10 mg of 1-ethyl-3-(3-dimethylamino-propyl)-carbodiimide, the tube was shaken at ambient temperature (20° C.) for 2 hours. Its contents were then transferred into a dialysis sack and dialysed at ambient temperature for 24 hours against 300 ml of BBS (three changes). One thus obtained a "Estapor"-HMD-p-hydrazino-benzoate support.

EXAMPLE 11

FIXATION OF A SIDE CHAIN CONSTITUTED BY A POLYAMINE COUPLED TO AN AROMATIC HYDRAZINE ONTO AN INSOLUBLE SUPPORT

To 7 mg of "Estapor"-spermine prepared as described in Example 2 above and having the formula:

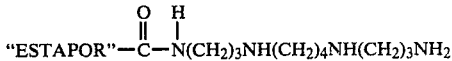

in suspension in 15 ml of BBS buffer of pH 8.1 were added 100μ moles of p-hydrazino-benzoic acid in aqueous solution. The mixture was shaken for 24 hours at ambient temperature (about 20° C.) in the presence of 0.05 M of EDC. Thereafter, the suspension was dialysed against BBS buffer of pH 8.8 until the O.D. at 230 nm was equal to zero.

EXAMPLE 12

FIXATION OF AROMATIC HYDRAZINE

To 10 mg of "Estapor" in the —NH₂ form (aromatic amine) in suspension in 10 ml of 0.1 M phosphate buffer of pH 7, is added 50μ moles of p-hydrazinobenzoic acid in solution in a 0.1 M borate buffer of pH 8. The mixture was shaken at 20° C. for 12 hours in the presence of 0.05 M of EDC. At the end of this time, one renewed the addition of EDC and continued the shaking for 12 hours. At the end of this second period, the suspension was centrifuged at 20,000 g for 1 hour and the residue taken up in 0.1 M borate buffer of pH 8.1 and recentrifuged to eliminate the p-hydrazinobenzoic acid which had not been coupled. This washing was followed by two other washings (0.01 M borate buffer of pH 8.1) then two washings with 0.1 M phosphate of pH 7. The obtained product was maintained in the last-mentioned buffer.

B1.2—CONSTITUTED BY ALIPHATIC HYDRAZINES

EXAMPLE 13

FIXATION OF A SIDE CHAIN COMPRISED BY AN ALIPHATIC DIAMINE COUPLED TO AN ALIPHATIC HYDRAZINE ON AN INSOLUBLE SUPPORT 6.0 mg of "Estapor"-HMD prepared as described in Example 1 above and having the formula:

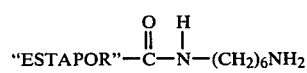

suspended in 0.1 M of phosphate buffer of pH 7 were shaken at 20° C. for 1 hour in the presence of glutaraldehyde at a final concentration of 1.25%. Thereafter, this suspension was dialysed against 0.1 M of phosphate buffer of pH 7.0 for 18 hours. To the suspension obtained after dialysis, were added 20$\mu$ moles of adipic dihydrazide in aqueous solution. The mixture was shaken for 16 hours at 20° C. and then dialysed to eliminate the excess of adipic dihydrazide.

B2—BINDING OF TERMINAL FUNCTIONAL GROUPS CONSTITUTED BY A PRIMARY AMINE FUNCTION

EXAMPLE 14

BINDING OF A SIDE CHAIN CONSTITUTED BY AN AMINO ACID COUPLED TO A DIAMINE ON A SOLID INSOLUBLE SUPPORT

Diaminopropane is bound to the "Estapor" beads which carry $\epsilon$-amino-caproic acid according to EXAMPLE 3, by the following procedure:

The contents of the dialysis bag were transferred to a tube containing 25$\mu$ moles of diaminopropane. The mixture was shaken for three hours at 20° C. in the presence of 0.05 M of EDC and then dialysed against a BBS buffer of composition 0.14 M NaCl, 0.01 M Borate-HCl, pH 8.8, the end of which the diaminopropane was coupled to the $\epsilon$-amino-caproic acid fixed on the insoluble support.

EXAMPLE 15

COUPLING OF HMD ON BEADS OF AGAROSE GEL CARRYING SIDE CHAINS OF $\epsilon$-AMINO-CAPROIC ACID The coupling of HMD onto the substituted "SEPHAROSE" beads of EXAMPLE 9, is effected according to the procedure described in EXAMPLE 7.

The —NH$_2$ terminals of the HMD substituent of the $\epsilon$-amino-caproic acid side chains were themselves coupled with an aliphatic or aromatic hydrazine which is substituted on the said —NH$_2$ terminal groups in accordance with two methods described respectively in EXAMPLE 11 and 13.

B3—BINDING ON A SOLID INSOLUBLE SUPPORT, OF SIDE CHAINS CARRYING TERMINAL FUNCTIONAL GROUPS COMPRISING SH—CH$_2$—CH—NH$_2$ GROUPS ABLE TO FORM A THIAZOLIDINE DERIVATIVE IN THE PRESENCE OF THE —CHO GROUP OF THE COMPOUND TO BE BOUND ON A SAID SUPPORT

EXAMPLE 16

FIXATION ON AN INSOLUBLE SUPPORT HAVING FREE —NH$_2$ GROUPS OF AN AMINO ACID HAVING —SH GROUPS

To 2 mg of "Estapor"-NH$_2$ in suspension in phosphate buffer of pH 6.5 were added 6$\mu$ moles of cysteine hydrochloride of formula HSCH$_2$CH NH$_2$COOH, HCl dissolved in water. The mixture was shaken at 20° C. for 16 hours in the presence of 0.05 M of EDC. Thereafter, the "Estapor" spheres on which the cysteine was fixed were washed on a 0.22$\mu$ Millipore filter to eliminate the excess cysteine and the reaction products. The spheres which had been modified in that way were again put in suspension in 2 ml of phosphate buffer of pH 6.5.

EXAMPLE 17

FIXATION OF CYSTEINE ON DOW 816 CARBOXYLATED POLYSTYRENE-HMD

To the suspension of Dow 816 carboxylated polystyrene-HMD obtained in EXAMPLE 6, are added 18 mg of cysteine-HCl dissolved in 2 ml of 0.1 M phosphate buffer of pH 6 and then EDC to a final concentration of 0.05 M. After 18 hours at 4° C., the spheres were washed as described in EXAMPLE 6 above.

EXAMPLE 18

EXAMPLES OF OXIDATION OF THE COMPOUNDS TO BE BOUND ONTO THE SUPPORTS

The determinating role of the oxidation according to the present invention, in the fixation of the oxidised compounds on the solid insoluble supports, is demonstrated in the following EXAMPLE 18.

EXAMPLE 18

DEMONSTRATION OF THE DETERMINATING ROLE OF FREE —CHO GROUPS OF GLOBULINS IN THE FIXATION OF THE LATTER ON AN INSOLUBLE SUPPORT

Gammaglobulins were oxidised as described but pre-reduced in the presence of NaB$^3$H$_4$ so that they are tritium-labelled and do not have free —CHO groups. Aliquots of these gammaglobulins (0.3 ml) containing 8400 cpm were put in contact with the samples set forth in the Table below in the presence of 0.1 M phosphate buffer of pH 6.0. After 16 hours at 4° C., the samples were filtered on a 0.22$\mu$ Millipore filter and washed four times with 5 ml of the following buffer:
0.1% Bovine Serum Albumin
0.1% Triton ×100
0.14 M NaCl, 0.01 M Borate-HCl pH 8.8

| Sample | Quantity | Volume | cpm retained on filter |
|---|---|---|---|
| (A) Buffer | — | 2 | 319 |
| (B) Estapor 68 | 500 $\mu$g | 2 | 311 |

| Sample | Quantity | Volume | cpm retained on filter |
|---|---|---|---|
| (C) Estapor $NH_2$ | 500 μg | 2 | 276 |
| (D) Estapor $NH-NH_2$ | 500 μg | 2 | 204 |

It appears from the results gathered in the foregoing Table that: (1) a certain quantity of radioactivity is retained on the filter; (2) the washing with the above-said buffer diminishes considerably the adsorption on the filters themselves. In the latter case, the adsorption on the filters due to the gammaglobulins+buffer alone represents approximately 20% of the total radioactivity of the aliquot (1:80 cpm) which remains on the filter; (3) the quantity of radioactivity retained on the filter is not increased significantly in the presence of "Estapor 68-COOH", of "Estapor 68-$NH_2$" or of "Estapor-NH-$NH_2$". In fact, the values are equal or less than the results obtained with the buffer alone (319 cpm). Thus, there is no adsorption of the gammaglobulins on the three types of "Estapor" used. Moreover, in order to make this filtration procedure significant, the radioactivity coupled to the insoluble supports in the presence of the oxidised gammaglobulins must exceed the 20% found with the nonoxidised gammaglobulins.

COMPARISON BETWEEN THE RADIOACTIVITY CONTENT ASSOCIATED WITH THE "ESTAPOR-$NH_2$", AND THE OXIDISED AND NON-OXIDISED GAMMAGLOBULINS AFTER REDUCTION WITH $NaB^3H_4$

| Reagents brought together | Volumes ml | Oxidised | Non-oxidised |
|---|---|---|---|
| ESTAPOR-$NH_2$ in 0.1M $PO_4$, pH 6.0 | 2.00 | 1 mg | 1 mg |
| Oxidised horse gammaglobulins | 0.10 | 2 mg | — |
| Non-oxidised horse gammaglobulins | 0.10 | — | 2 mg |
| 0.1M Borate, pH 8.8 | 0.90 | + | + |
| $NaB^3H_4$ in $H_2O$ | 0.20 | 2 μCi | 2 μCi |

After contacting during 18 hours at 4° C., the content of each bag is dialysed during 5 days against BBS pH 8.8 with three or four changes per day, until the dialysis liquid contains no more radioactivity. An aliquot of each preparation is then filtered on Millipore 0.22μ and washed with the buffer 0.1% SAB, 0.1% Triton×100, BBS pH 8.8.

The optical density at 550 nm is measured on another aliquot in order to find the "Estapor" concentration.

| Sample | cpm/mg |
|---|---|
| Estapor 68-$NH_2$—oxidised gammaglobulin | 62 466 |
| Estapor 68-$NH_2$ non-oxidised gammaglobulin | 11 135 |

The radioactivity found with Estapor 68-$NH_2$ in the presence of non-oxidised gammaglobulins represents only 17.8% of the radioactivity found in association with the Estapor 68-$NH_2$ in the presence of oxidised gammaglobulins. (This value is of the same magnitude as the value due to the adsorption of gammaglobulins on filters in the absence of Estapor).

On the other hand, with the oxidised gammaglobulins the quantity or radioactivity associated with Estapor-$NH_2$ increases five times.

Some examples of oxidation of various compounds containing carbohydrate residues, by oxidation of at least one of their —$CH_2OH$ groups in —CHO groups, will be given hereafter.

A. OXIDATION OF GAMMAGLOBULINS

EXAMPLE 19

CHEMICAL OXIDATION OF GAMMAGLOBULINS IN SOLUTION

Gammaglobulins obtained from the goat, the rabbit and the horse were purified by $(NH_4)_2SO_4$ precipitation followed by chromatography on DEAE-cellulose.

To 60 mg of horse immunogammaglobulins (containing antipolyamine antibodies) in solution in 2 ml of 0.1 M phosphate buffer of pH 6 were added 0.2 ml of 0.15 M $NaIO_4$ soluble in water.

The mixture was left at 4° C. and protected from light for 3 hours, then dialysed against a 0.14 M NaCl-0.1 M phosphate buffer of pH 6 for 1 hour, with three changes. At this pH, th risk of formation of Schiff bridges between the reactive aldehyde groups obtained by oxidation by $NaIO_4$ and the —$NH_2$ groups, be it those of lysine or of terminal amino groups of proteins is reduced.

EXAMPLE 20

CHEMICAL OXIDATION OF ANTIGAMMAGLOBULINS-ANTIBODIES

To 520 μg of goat anti-rabbit gammaglobulins in 0.1 ml of BBS where added 0.1 ml of 0.03 M $NaIO_4$. The mixture was left at 4° C., protected from light, for 3 hours and then dialysed against BBS for 2 hours with three changes of buffer.

EXAMPLE 21

CHEMICAL OXIDATION OF GAMMAGLOBULINS

To 60 mg of horse immunoglobulins in solution in 2 ml of 0.1 M phosphate buffer of pH 6 were added 0.2 ml of 0.15 M $NaIO_4$ soluble in water.

The mixture was left at 4° C. protected from the light for three hours at the end of which the action of the $NaIO_4$ was arrested by addition of glycerol to a final concentration of 0.15 M. After 30 minutes at 4° C., the reaction products were dialysed at 18 hours at 4° C. with several changes against 0.1 M phosphate buffer of pH 6.

B. OXIDATIONS OF VIRUSES

EXAMPLE 22

PREPARATION OF OXIDISED MEASLES VIRUS

To 5 ml of an antigenic preparation of measles virus containing 16 mg of protein were added 0.5 ml of 0.15 M $NaIO_4$ in a 0.1 M sodium phosphate buffer of pH 6.

This mixture was left at 4° C. and protected from the light for 3 hours.

0.5 ml of 0.15 M $Na_2SO_3$ was then added to arrest the action of the $NaIO_4$.

After 30 minutes at 4° C., the mixture was dialyzed for 18 hours at 4° C. in order to eliminate the excess oxidation products.

EXAMPLE 23

PREPARATION OF OXIDISED CANINE DISTEMPER VIRUS

The procedure carried out for oxidising the Canine Distemper virus is that which is described in the foregoing Example 22.

EXAMPLE 24

PREPARATION OF OXIDISED INFLUENZA VIRUS

The procedure carried out for oxidising the influenza virus is that which is described in the foregoing Example 22.

EXAMPLE 25

PREPARATION OF OXIDISED GERMAN MEASLES VIRUS

The procedure carried out for oxidising the German Measles virus is that which is described in the foregoing Example 22.

C/OXIDATION OF HORMONES

EXAMPLE 26

PREPARATION OF OXIDISED HUMAN CHORIONIC GONADOTROPHIN (HCG)

The procedure carried out for oxidising this hormone is that described in the foregoing Example 19 and 20.

III.—EXAMPLES OF COUPLING OF COMPOUNDS CONTAINING CARBOHYDRATE RESIDUES AT LEAST ONE —$CH_2OH$ GROUP OF WHICH HAS BEEN OXIDISED TO A —CHO GROUP, ON THE SUPPORTS OF THE INVENTION

EXAMPLE 27

EXAMPLE OF COUPLING EFFECTED ON A TERMINAL —$NH_2$: PREPARATION OF "ESTAPOR"-HMD-ANTIPOLYAMINE ANTIBODY REAGENT BY FIXING ANTIBODIES ON THE SUPPORT

To prepare a reagent according to the invention using antipolyamine antibodies, which are utilised elsewhere for research and for estimating polyamines in the blood of patients, one fixes these antibodies by substrate affinity chromatography on glass supports containing spermine then one oxidises them with an 0.06 M solution of $NaIO_4$. After 30 minutes at 4° C. in darkness, the antibodies are washed in BBS buffer of pH 8.8 in order to eliminate excess $NaIO_4$.

2 ml of "Estapor"-HMD (10 mg) (prepared as indicated in Example 1 above) were mixed with the oxidised antibody. The suspension was shaken gently by a rotary movement at 4° C. for 14 hours. The Schiff-bases so formed were stabilised by treatment for 5 hours at 4° C. with $NaBH_4$ (3μ moles) under intermittent agitation. The supernatant was recovered, the residue was rewashed four times with BBS and all the supernatants were reunited.

EXAMPLE 28

EXAMPLE OF COUPLINGS EFFECTED ON A HYDRAZINE: PREPARATION OF REACTIVE "ESTAPOR"-HMD-P-HYDRAZINOBENZOATE-ANTI IgG ANTIBODIES

"Estapor"-rabbit anti IgG antibodies, which constitute a utilisation model using antibodies in solution, were prepared. The final preparation presented a very large spectrum of utilisation because it allowed all immunological reactions in which rabbit IgG are used to be detected by the indirect method.

0.1 ml of the solution obtained in Example 20 (260 μg) where then added to 1.7 mg of "Estapor"-HMD-p-hydrazinebenzoate. The mixture was shaken for 3 hours at 4° C.

As in Example 27 above, after the described treatment, the beads of "Estapor" containing the antibodies were washed and concentrated by sedimentation on a layer of 60% sucrose through a solution of 10% sucrose (100 000 g for 1 hour at 4° C.). The "Estapor" concentrated at the interface and was dialysed to eliminate the excess sucrose.

EXAMPLE 29

EXAMPLE OF COUPLING EFFECTED ON A TERMINAL —SH: COUPLING OF AN INSOLUBLE SUPPORT HAVING FREE TERMINAL —SH GROUPS TO —CHO GROUPS OF OXIDISED GAMMAGLOBULINS

To 2 mg of "Estapor-SH" were added 1 mg of oxidised gammaglobulins as described in Example 10. After 30 minutes of contact at 4° C., one observed a floculation of the "Estapor-SH" particules by formation of thiazolidines. This floculation is not produced with "Estapor-$NH_2$" nor with "Estapor—SH" on which one has fixed non-oxidised gammaglobulines.

IV.—EXAMPLES OF ISOTOPIC LABELLING OF THE PRODUCTS OF THE INVENTION

EXAMPLE 30

PREPARATION OF RADIOACTIVE COUPLED PRODUCTS ACCORDING TO THE INVENTION BY PRE-LABELLING THE LATEX-SUPPORT WITH $^3H$ OR $^{14}C$ ETHANOLAMINE

Beads of "Estapor" were rendered radioactive by covalently binding $^3H$ or $^{14}C$ ethanolamine to them. To 20 mg of the "Estapor" in suspension in BBS were added 0.05 ml of $^{14}C$ ethanolamine, 10μ Ci (1.6μ Mole) and 6.0 mg of 1-ethyl-3-(3-dimethyl-aminopropyl)-carbodiimide in a total volume of 4.0 ml. After rotary shaking for 2 hours at 20° C., 20μ moles of 1-ethyl-3-(3-dimethyl-aminopropyl)-carbodiimide were added. The agitation was maintained for 2 hours then the contents of the tube were dialysed against BBS until free radioactivity had been eliminated.

The obtained product had a radioactivity of $2.2\times10^6$ cpm per mg of "Estapor".

The fixation of antibodies was effected as described in Example 27. The obtained product corresponded thus to a highly radioactive antibody preparation in which the antibody has not sustained any chemical manipulation other than the fixation to latex of the carbohydrate moiety. The product can be used in all applications of radioimmunological determination which use direct or indirect methods. The measurement of the reaction may be carried out by determining the radioactivity either of the agglutinated antigen-antibody complex, or of the unreacted beads, the separation being effected by centrifugation or filtration.

These reagents (radioactive) allow the quantitative measurement of antigens on the surface of cells to be done by counting the radioactivity adhering to the slides. Thus, it is possible to quantify the data previously obtained when the beads were visualised under the scanning electron microscope.

In so far as it concerns the products derived from the coupling of glyco-proteins and more particularly antibodies to supports comprising at least one reactive —$NH_2$ through the intermediary of a carbohydrate residue, which have been described in a non-limiting manner in Examples 27 and 28, there is available thanks to the present invention, a range of beads containing antibodies which are specific for different antigens of interest to medical pathology and which allow rapid and easy serum diagnosis of a wide range of illnesses. The use of beads containing antibody antigammaglobulins again widens the scope of their use in introducing the indirect procedure. Quantification is easy and precise either by the direct dilution method or by the competitive method.

The procedure can be applied to all dosages (hormones, medicaments etc.) based on an immunological reaction. The use of radioactive beads renders the process as sensitive as all the other radioimmunological methods while diminishing at the same time the risk of modifying the antibodies or antigens in the course of their iodination.

The described method presents, compared to currently utilised procedures (radioimmunological dosage, fluorescence, free radical estimation, immunoenzymological dosage, etc.), the following advantages: ease of use without necessitating particular equipment; sample manner of use thus no long training periods are required; good sensitivity; stability of reagents which can be kept for many months; and very low price.

EXAMPLE 31

PREPARATION OF LABELLED COUPLED PRODUCTS BY ISOTOPIC LABELLING OF ANTIBODIES

I.—LABELLING WITH TRITIUM

To 1.5 mg of goat antipolyamine gammaglobulins in 2 ml. of 0.14 M NaCl, 0.02 M phosphatic buffer at pH 6 were added 0.65 ml of 0.06 M $NaIO_4$ in solution in a phosphate buffer of pH 6 (final concentration of $NaIO_4$: 0.015 M).

The mixture was left at 4° C. and protected from light for 3 hours and then dialysed against a 0.14 M NaCl, 0.02 M phosphate buffer of pH 6 for 1 hour with three changes, to eliminate excess $NaIO_4$ (verified with the aid of starch-iodide paper).

At this pH, the risk of forming Schiff's bases between the reactive —CHO aldehyde groups thus formed and the —$NH_2$ groups, either of lysine or of terminal —$NH_2$ groups of proteins, is reduced.

The contents of the dialysis sack was then transferred to a tube.

An excess of crystalline $NaB^3H_4$ (100 mCi/mMol obtained from New England Nuclear) was then added, followed by 1 ml of 0.1 M berate-HCl buffer of pH 8.8 (this change of pH favours the reduction of —CHO groups to $CH_2OH$ groups). After a contact time of 16 hours at 4° C., under a well ventilated hood, the contents of the tube were transferred to a dialysis bag and dialysed until the dialysis liquid was free of all radioactivity. One thus obtained a labelling of the antipolyamine antibodies of 670 cpm per μg of proteins.

It is also possible to increase the specific activity of the antibodies in the following fashion:—to 1.5 mg of oxidised gammaglobulins were added 20μ Ci of $^3H$ ethanolamine (3.8 Ci/mMol) at a pH of 8.8; the Schiff's base thus formed were then stabilised by reduction with $NaB^3H_4$ (5 mCi) for 18 hours at 4° C. the excess of $NaB^3H_4$ was eliminated by dialysis. This allowed one to obtain anti-polyamine gammaglobulins having a specific activity of 1807 cpm/μg.

$^{14}C$ labelled antibodies can be obtained by a similar procedure but using $^{14}C$ ethanolamine instead of $^3H$ ethanolamine and carrying out the reduction with $NaB^3H_4$.

II—Coupling of a solid insoluble support carrying side chains bearing at least one reactive —$NH_2$ to the —CHO groups of oxidised gammaglobulins and stabilisation and lebelling of the Schiff's base so formed, by reduction with $NaB^3H_4$. The techniques used were those described in Examples 27 and 29 above.

As a result reagents were obtained which are of very long stability, which did not emit gamma rays (contrary to known procedures which rely on labelling by iodination of tyrosine groups in the protein chain, using radioactive iodine) and in which the biological activity is unaltered.

V.—EXAMPLES OF IMMUNO-REAGENTS

EXAMPLE 32

PREPARATION OF A DIAGNOSTIC REAGENT FOR MEASLES CONSTITUTED BY A PRODUCT DERIVED FROM THE REACTION OF A SUBSTITUTED SUPPORT WITH OXIDISED MEASLES VIRUS

I.—PREPARATION OF SUBSTITUTED COLOURED SUPPORT (a) The attachment of a side chain carrying terminal —$NH_2$ groups constituted by a diamine is realised according to the procedure described in Example 1 above.

(b) The fixation onto "ESTAPOR-$NH_2$" obtained in the preceding step, of an amino acid having an —SH group is effected using the procedures describes in Example 16 above.

II.—PREPARATION OF OXIDISED MEASLES VIRUS

The oxidation of this virus is performed as described in the foregoing Example 20.

III.—COUPLING OF MEASLES VIRUS ON "ESTAPOR-SH"

To 20 mg of "ESTAPOR-SH" obtained in step Ib above in suspension in a 0.1 M phosphate buffer of pH 6.0 were added 10 mg of oxidised measles virus as described in II above.

The mixture was stirred at 4° C. for 18 hours. It was then centrifuged at 6000 g for 60 minutes. The supernatant was recovered and the residue washed twice with a phosphate buffer of pH 6.0.

The amount of protein remaining in the supernatant allowed one to determine that 130 μg of viral protein had been fixed per mg of "ESTAPOR-SH"

EXAMPLE 33

PREPARATION OF A DIAGNOSTIC REAGENT FOR CANINE DISTEMPER VIRUS DISEASE CONSTITUTED BY THE PRODUCT OF THE REACTION BETWEEN A SUBSTITUTED SUPPORT WITH OXIDISED CANINE DISTEMPER VIRUS

The preparation of this diagnostic reagent was effected by the procedure corresponding to that described in Example 32 I-II-III.

This reagent was tested under the conditions described in Example for "ESTAPOR" measles no agglutination was obtained in the presence of a rabbit serum anti Canine distemper virus.

EXAMPLE 34

PREPARATION OF A DIAGNOSTIC REAGENT SPHERES OF LATEX-INFLUENZA VIRUS

The technique used for the preparation of this reagent was that described in Example 32 above, the measles virus being replaced with influenza virus.

EXAMPLE 35

PREPARATION OF A DIAGNOSTIC REAGENT SPHERES OF LATEX-GERMAN MEASLES VIRUS

The same technique was used to prepare this reagent as that described in Example 32 for the preparation of diagnostic reagent for measles, but replacing the measles virus with German measles virus.

EXAMPLE 36

PREPARATION OF A DIAGNOSTIC REAGENT SPHERES OF LATEX-CYTOMEGALIC VIRUS

To prepare this reagent the same technique was used as that described in Example 32 but replacing the measles virus but with cytomegalic virus.

EXAMPLE 37

PREPARATION OF "ESTAPOR" ANTIBODY DIAGNOSTIC REAGENT

I.—PREPARATION OF THE SUBSTITUTED SUPPORT

The fixation on latex beads of a side chain having terminal —NH₂ groups and the fixation on this chain of an amino acid having —SH groups were effected as described in Example 32.

II.—THE CHEMICAL OXIDATION OF THE GAMMAGLOBULIN IS PERFORMED AS DESCRIBED IN EXAMPLE 21

III.—COUPLING OF OXIDISED GAMMAGLOBULINS ON "ESTAPOR"-SH OBTAINED IN STEP I

This coupling was carried out according to the technique described in Example 29 above. By this technique, the coupling of gammaglobulins containing antipolyamine antibodies, gammaglobulins anti human fibrin degradation products (FPD) gammaglobulins anti human IgG, gammaglobulins anti human IgM, gammaglobulins anti rabbit IgG and gammaglobulins- anti guinea pig IgG, have been achieved.

EXAMPLE 38

PREPARATION OF "ESTAPOR"-HUMAN CHORIONIC GONADOTROPHIN (HCG)

I.—PREPARATION OF SUBSTITUTED ESTAPOR

The binding on latex beads of a side chain having terminal —NH₂ groups and the attachment onto this chain of an amino acid having an —SH group were carried out as described in Example 16 above.

II.—PREPARATION OF OXIDISED HUMAN CHORIONIC GONADOTROPHIN

The oxidation was carried out in accordance with the technique described for gammaglobulins in Example 26 above.

III.—COUPLING OF ESTAPOR-SH TO CHORIONIC GONADOTROPHIN

This coupling was carried out in accordance with the technique described in Example 29 above.

The effectiveness of the diagnostic reagents thus obtained is demonstrated in the following Chapter VI.

VI.—EFFICIENCY OF THE IMMUNOREAGENTS OF THE INVENTION

The antigen antibody reaction is effected under conditions of temperature, duration of contact etc., the most appropriate to each particular case. The positive reactions manifest is themselves by agglutination of the beads. Determining the results is effected by estimating the agglutination either simply by macroagglutination or by microagglutination on alveolar plates. It is possible to quantify the reaction either by direct nephelometric measurement or by centrifugation and visualization of the optical density of the remaining latex spheres, or by measurement of the radioactivity in the case of labelled latexes present either on the filters or in the residue.

A/TESTS OF MACROAGGLUTINATION ON GLASS PLATES

EXAMPLE 39

TEST OF AGGLUTINATING ACTIVITY OF "ESTAPOR—SH"-OXIDISED MEASLES VIRUS

The dilutions of antiserum were effected in the following buffer: 1% bovine serum albumin, 0.14 M NaCl: 0.01 M Tris-HCl at pH 8.2. The reactive latex-measles virus reagent prepared according to the invention was also used in this test at a rate of 675 µg/ml.

Figure 4:
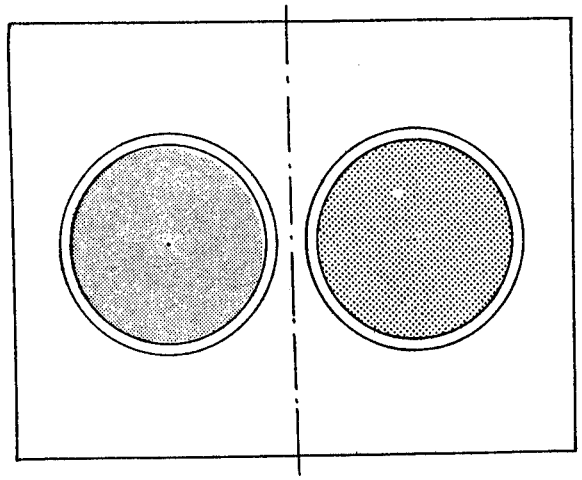

The results obtained by macroagglutination on glass plates are illustrated in FIG. 4 in which the results obtained with the control (rabbit serum anti VSV) appear in the left hand side of the figure and the results obtained with the rabbit serum anti measle, are found on the right hand side of the figure.

EXAMPLE 40

TEST OF AGGLUTINATING ACTIVITY OF "ESTAPOR-SH"-OXIDISED CANINE DISTEMPER VIRUS

This reagent has been tested in the conditions reported in Example 39 above.

Similar results have been obtained in the presence of rabbit serum anti-VSV as control, and of rabbit serum anti-Canine Distemper virus as the sample tested.

EXAMPLE 41

TEST OF AGGLUTINATING ACTIVITY OF ESTAPOR-HCG BY MACROAGGLUTINATION ON A PLATE

Results: The reaction was positive with a rabbit anti-HCG serum diluted to 1/160. At this dilution, inhibition of the reaction was obtained with the urine of a pregnant woman.

EXAMPLE 42

TEST OF ACTIVITY OF REACTIVE SPHERES OF DOW-LATEX-ANTI-FIBRINOGEN BY MACROAGGLUTINATION ON PLATES

Figure 5:
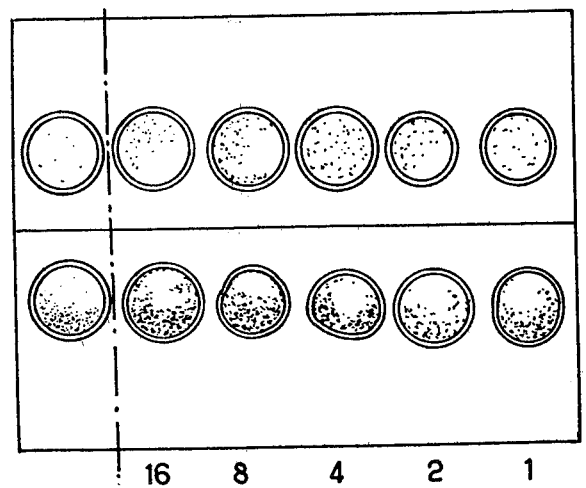

The spheres of Dow anti-FDP were suspended in the following buffer: 1% bovine serum albumin; 0.14 M NaCl; 0.1 M Tris-HCl at pH 8.2; 0.0015 M sodium azide at a concentration of 8 mg/ml. The reaction was positive with human fibrinogen at 4 $\mu$g/ml and as shown in the attached FIG. 5 and also with human serum diluted 1/10.

EXAMPLE 43

DETERMINATION OF THE POLYAMINE CONTENT IN URINE BY MACROAGGLUTINATION ON GLASS PLATES

The spheres of "Estapor"-polyamine prepared as described in Example 2 above, are suspended in a buffer containing 1% bovine serum albumine, 0.14 M NaCl, 0.1 M Tris, pH 8.3, 0.0015 M sodium azid, at a concentration of 4 mg latex/ml.

A positive agglutination has been obtained with an antipolyamine goat serum diluted to 1/30 rd in the same buffer; the negative reaction has been obtained with the same goat serum, before immunisation.

In those conditions, the positive reaction has been inhibited by the urin of pregnant woman.

B/ TESTS BY MICROAGGLUTINATION ON ALVEOLAR PLATES

EXAMPLE 44

TEST OF THE MICROAGGLUTINATION ACTIVITY OF "ESTAPOR-SH"-OXIDISED MEASLES VIRUS

Figure 3:
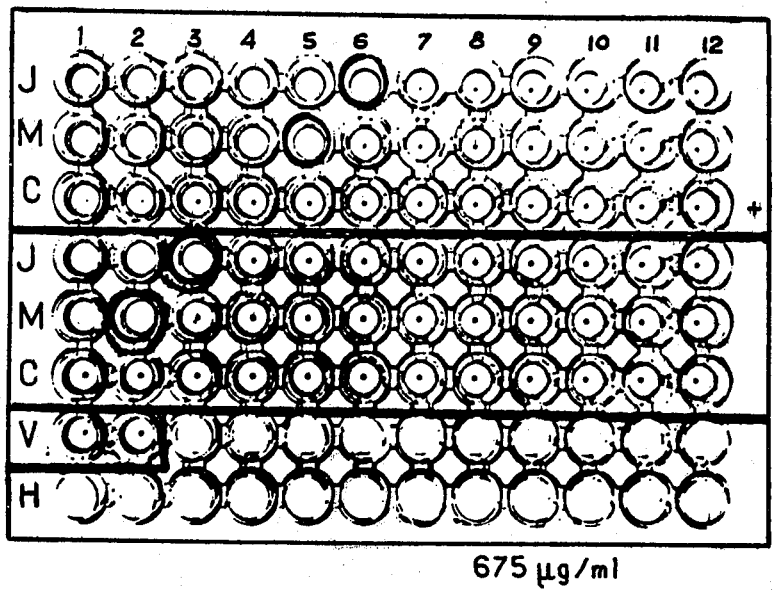

The results obtained using coloured Estapor prepared according to Example are shown in FIG. 3 of the attached drawings.

The antiserum dilutions were effected in the following buffer: 0.14 M NaCl, 0.01 M borate-HCl of pH 8.1.

A: Serum of rabbit J anti-measles prepared on Vero cells;

B: Serum of rabbit M anti-measles prepared on Vero cells;

C: Serum of rabbit B anti-VSV (VSV=Vesicular Stomatitis Virus) used as control.

The dilution of serum was as follows:

| Sample 1 1/10 | Sample 5 1/160 | Sample 9 1/2560 |
|---|---|---|
| — 2 1/20 | — 6 1/320 | — 10 1/5120 |
| — 3 1/40 | — 7 1/640 | — 11 1/10240 |
| — 4 1/80 | — 8 1/1280 | |

Sample 12 contained only buffer.

The reagent latex-measles virus according to the invention was used at a rate of 675 $\mu$g/ml.

The reaction was positive for $A_1$ to $A_6$ and negative for $A_7$ to $A_{12}$.

The reaction was positive for $B_1$ to $B_5$ and negative for $B_6$ to $B_{12}$.

The reaction was negative for $C_1$ to $C_{12}$.

Figure 2:
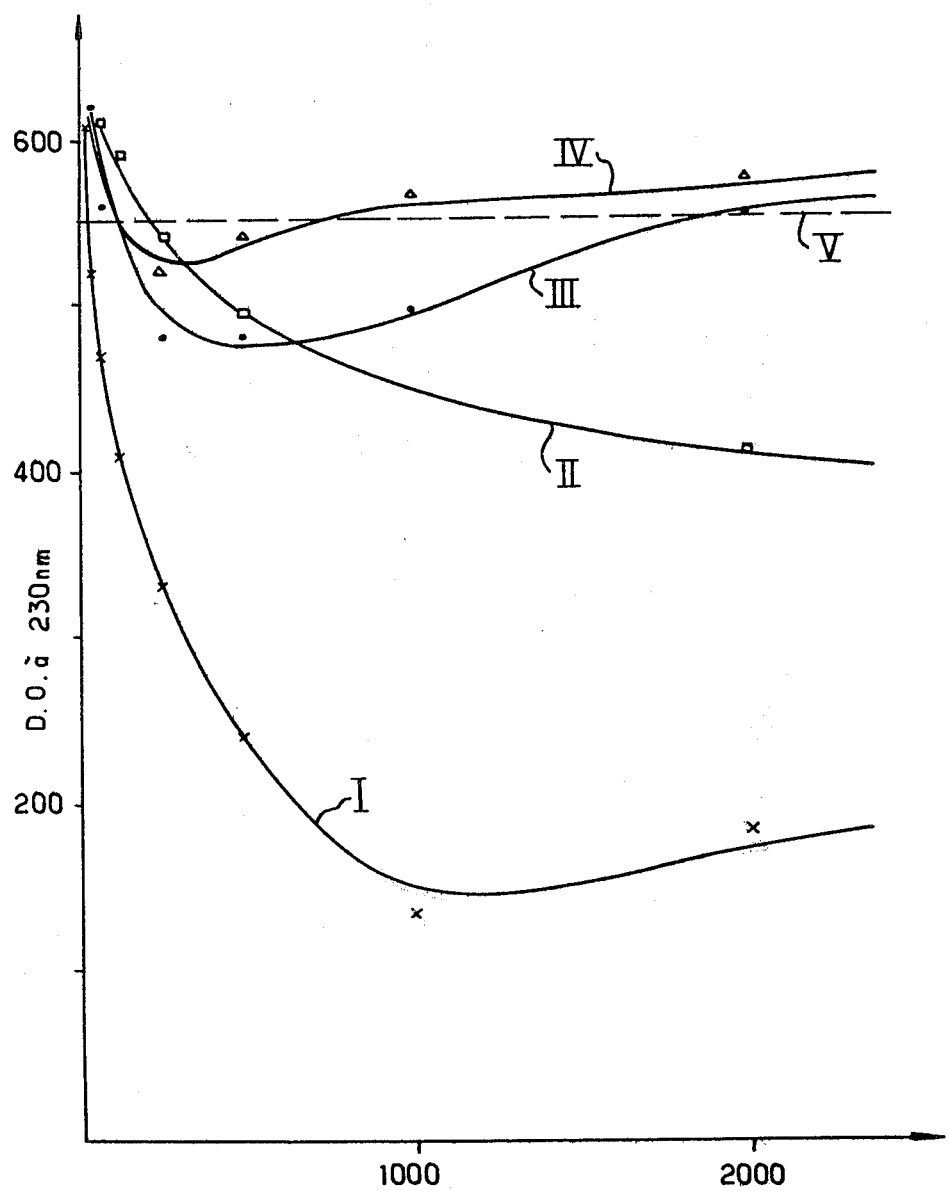

It may be seen from the test illustrated in FIG. 2 that the three controls $A_{12}$, $B_{12}$, $C_{12}$ are negative and that there is no non specific reaction with serum C.

The sensitivity of the reaction has been increased by submitting the latex spheres-measles virus according to the invention to a preliminary treatment with tritium X-100 at 1%: with the triton treated latex measles, the negative reaction with serum J does not start until $A_{10}$ and with serum M until $B_6$. The reaction with serum C is totally negative. This sensitivity of reaction has been controlled by the tests with latex-Vero (that is to say an extract of Vero cells used to prepare the measles virus and coupled to latex under the conditions described in III of the present examples. There is not any reaction between the reactive latex-Vero and the sera J, M and C which allows one to conclude that the reaction with the reactive latex-measles reagent prepared according to the invention is specific and of a high sensitivity.

C/ QUANTIFICATION OF THE DIAGNOSTIC REACTION BY DIRECT NEPHELOMETRIC READING

EXAMPLE 45

DIRECT MEASUREMENT BY NEPHELOMETRY FOR OXIDISED GAMMAGLOBULINS COUPLED ONTO THE SUPPORTS OF THE INVENTION

To obtain a direct agglutination reaction of antipolyamine supports with antigens, one adds a fixed quantity of the reagent "Estapor"-antipolyamine of Example 37, namely 2 $\mu$g/ml in 0.1% of Triton $X_{100}$-BBS buffer of pH 8.1 of known quantities (15 to 500 nanograms/ml of antigens). The mixture is left in contact for 45 hours. The light diffused at 90° by the mixture is measured. The results obtained are shown in FIG. 1 by Curve I for the normal rabbit gammaglobulins as one antigen and by Curve II for the acid poly L glutamic spermine as the other, the quantities of antigen introduced being shown on the abscissa and the light diffused at 90° on the ordinates. The sensitivity and the precision of measurement are of the order of nanograms.

EXAMPLE 46

TEST OF ACTIVITY OF A DIAGNOSTIC REAGENT "ESTAPOR" ANTICORPS BY NEPHELOMETRY

Dilutions of antigens and of latex antipolyamine antibodies were effected in "Borate BBS" buffer which had been filtered on a 0.22 $\mu$ "Millipore" filter (Borate Buffer Saline=0.01 M $Na_2B_4O_7$, 0.15 M NaCl, HCl at pH 8.1). After bringing into contact the reagents, the test samples and the controls were incubated for one hour at 37° C. then at ambient temperature.

Equilibrium was then attained at the 45th hour of incubation in the case of 0.1 n mole of spermine coupled to of poly-L-glutamic acid (P.L.G. Spm) in the presence of 2 $\mu$g of latex-antipolyamine (latex coupled to antibodies from goats immunised against polyamines).

The specificity of this reaction has been shown by comparing the agglutination reactions obtained in the presence of P.L.G. Spm antigen with latex-antipolyamine on one hand and latex coupled to rabbit globulins as control on the other.

The application to the measurement of antigen necessitates the determination of the equivalent point: which is the maximum increase of diffused luminous intensity as a function of the ratio: latex-antibody/antigen.

This affinity at the equivalent point is a constant for a given batch of latex-antibodies. It allows, knowing the concentration of latex-antibody at the point of equivalence the deduction of the concentration of unknown antigen present.

In practice, when confronted with a preparation of an antigen of unknown concentration, it is preferable to make a range of concentrations of latex-antibody.

On can prepare a control series and a series receiving a constant quantity of antigen.

I is the diffused luminous intensity for the controls. I' is the diffused luminous intensity for the test samples containing antigen.

I is a linear function of the concentration of latex-antibody in the tested region: from 62.5 ng of 8 µg/ml.

At each point of the range the ratio I'/I% translates the aggregation phenomenon of latex spheres in the presence of the corresponding antigen.

In the case of a preparation of latex coupled to globulins of goats immunised against human fibrinogen for 0.35 ngm of fibrinogen in the presence of variable concentrations of latex-anti-fibrinogen, the equivalent point is attained for 200 mg of latex anti-fibrinogen, that which corresponds to a ratio latex-antibody/antigen of 570. This preparation permits the estimation of a minimum quantity of 70 pg of human fibrinogen with sufficient precision. The ratio at the equivalence point does not vary in a notable fashion in the course of keeping a preparation of latex-antibody for several months at 4° C. This is probably due to the covalent bonding of the antibody to the latex and to the elimination after the binding of antibodies which were simply adopted.

D/ QUANTIFICATION OF THE DIAGNOSTIC REACTION BY READING OF THE OPTICAL DENSITY

EXAMPLE 47

To effect a direct agglutination reaction of "Estapor"-antipolyamines with polyamines, one adds a fixed quantity of "Estapor"-antipolyamines (6 µg), prepared according to Example 27 above increasing quantities (from 31 to 2 000 nmoles) of antigens (spermine, spermidine, putrescine linked to poly-L-glutamic acid and lysine HCl). The mixture is left for 30 minutes at 25° C. then overnight at 4° C. After centrifugation at 3 000 rpm for 15 minutes to sediment the "Estapor" beads and the antigen which is fixed to them, the optical density of the supernatant is measured at 230 nm. The results obtained are shown in FIG. 2, which represents, in the order of reaction, curves I for spermine, II for spermidine, III for lysine, IV for putrescine and V for the blank, with a limit of detectability for spermine of 32 n moles, the optical density being shown on the ordinates and the quantity in n moles of antigens added on the abscissa.

E/QUANTIFICATION OF THE DIAGNOSTIC REACTION BY MEASUREMENT OF THE RADIOACTIVITY OF LABELLED LATEXES

EXAMPLE 48

The excellent sensitivity of reagents prepared according to the present invention has been demonstrated in the course of a comparative study of agglutination carried out respectively with coupled products such as those described by R. S. MOLDAY et al in the prior art (references cited above) and with the radioactive coupled products obtained according to Example 30 above, which will be reported below.

COMPARATIVE STUDY OF AGGLUTINATION OF COUPLING PRODUCTS ACCORDING TO MOLDAY ET AL OF ONE PART AND ACCORDING TO THE INVENTION OF THE OTHER PART

I.—Some spherical carboxylated polystyrene beads of 0.30µ (reference PSI 68 of Rhone-Progil) rendered radioactive $^{14}C$ labelled ethanolamine were substituted with hexamethylenediamine according to Example 1 and then activated by reaction with 1.25% glutaraldehyde for 1 hour at ambient temperature (20° C.), after which they were subjected to prolonged dialysis to eliminate the excess glutaraldehyde.

The substituted beads so obtained were estimated at 560 micrograms of beads per ml and their radioactivity was 95 000 cpm per ml.

520 micrograms of goat antibodies to rabbit antigammaglobulin were added to it and left in contact therewith with agitation for 5 hours at ambient temperature (20° C.).

II.—Some 0.30µ PSI 68 beads which had been prefiltered on a filter and labelled with $^{14}C$ ethanolamine were substituted according to Example 10 above with hexamethylenediamine and p-hydrazino-benzoic acid. 560 micrograms of substituted beads were obtained in this manner per ml and their radioactivity evaluated at 87 000 cpm per ml.

To them was added 0.15 ml (i.e. 520 micrograms) of goat antibody to rabbit antigammaglobulin which had been previously oxidised with sodium periodate according to the present invention.

In the two cases, the bead-antibody complexes were separated from free antibody by centrifugation across a layer of 10% sucrose, the excess sucrose being eliminated by dialysis.

III.—Comparative study proper

Preparations I and II above were then treated as follows:

A/To 0.15 ml of each of the two preparations were added:
0.25 ml of 2% decomplemented calf serum
0.1 ml of rabbit serum at the following dilutions:
1/500
1/1 000
1/5 000
1/10 000

B/The composition of the controls was as follows:
0.15 ml of each of preparations I and II
0.25 ml of 2% decomplemented calf serum
0.1 ml of BBS buffer of pH 8.8.

The four tubes of the experimental series A and the tube of the control series B for each preparations I and II were incubated at 4° C. for 48 hours, then 0.4 ml of each tube was filtered across a 0.80µ Millipore filter presaturated with 2% decomplemented calf serum. The filters were washed with 4×2 ml of 2% calf serum followed by 10 ml of BBS buffer and then followed by 4×2 ml of BBS buffer.

The filters were counted in 10 ml of a mixture of Triton × 100/toluene 1:2 vol/vol.

The results obtained are set forth in the following Table.

TABLE

| Preparation | Maximum reactivity retained on the filter, with sarum diluted to | Progressive Diminution of the radioactivity at dilutions | | | Equivalence Point |
|---|---|---|---|---|---|
| I | 90 cpm dilution to 1/500 | 1/1000 | 1/5000 | 1/10000 | 1/500 |
| II | 113 cpm dilution to 1/5000 | 1/500 | 1/1000 | | 1/5000 |

It can be seen from the Table that: Compared to the fixation procedure according to the present invention, for which an equivalence point of 1/5000 was obtained, the fixation of antibodies on latex particles according to the technique of MOLDAY et al, for which an equivalence point of 1/500 was obtained implies that coupling by the latter technique brings about an important loss of sensitivity.

It results from the preceding that, whichever may be the ways of carrying out, of performing and of application adopted, there are obtained products resulting from the coupling of compounds containing carbohydrate residues, through their —CHO group(s), with solid, insoluble supports bearing side chains carrying at least one reactive —$NH_2$ which reacts with the said —CHO group, to give rise to the said coupled product, which products can be used, notably as diagnostic reagents having a great stability and a very high sensitivity.

What I claim is:

1. A process for agglutinating a biologically active analyte to an immunochemical reagent comprising
   forming on an insoluble support base a side chain having from three to ten carbon atoms and at least one reactive —$NH_2$ group, by reacting a compound selected from the group consisting of di-amines, polyamines, amino-acids, aliphatic hydrazines bearing an acid group, and aromatic hydrazines bearing an acid group with an insoluble support base bearing at least one carboxyl group or at least one amino group in the presence of a condensation agent to covalently bind said compound to said support base to form a side chain on said insoluble support base;
   oxidizing into a CHO group at least one —$CH_2OH$ group of an organic compound having a carbohydrate residue; attaching the organic compound to said support by reacting said —CHO group with at least one reactive —$NH_2$ on said side chain to chemically attach the organic compound on said support; and
   combining said analyte and said support under conditions suitable for agglutination.

2. A process according to claim 1, in which the compound covalently bound to the insoluble solid support is a diamine.

3. A process according to claim 2, in which the diamine is selected from the group consisting of hexamethylenediamine and diaminopropane.

4. The process of claim 1, further comprising coupling a nitrogen containing compound having from 3 to 10 carbon atoms and at least one reactive —$NH_2$, to said side chain; said nitrogen containing compound selected from the group consisting of aliphatic amines, aromatic amines, aliphatic hydrazines, aromatic hydrazines and amino acids, to form a longer side chain containing at least one reactive —$NH_2$.

5. The process of claim 4, wherein said nitrogen containing compound is an amino acid containing both an $NH_2$ and a —SH group capable of forming a heterocyclic in the presence of the CHO group of the organic compound to be attached.

6. The process of claims 1, 4 or 5, wherein when said reactive $NH_2$ is a terminal primary amine group, stabilizing the resulting Schiff base by chemical reduction.

7. The process of claim 4, wherein said coupling is performed in the presence of a coupling agent.

8. A process according to claims 1 or 7, wherein said condensation and said coupling agents are selected from the groups consisting of glutaraldehyde, N-hydroxylsuccinimide and a totally or partially water-soluble carbodiimide of the general formula R—N=C=N—R in which R represents an alkyl radical having 2 to 12 carbon atoms; a cycloalkyl radical having 5 or 6 carbon atoms; a mono-aryl substituted lower alkyl radical; a monoaryl radical; a lower alkyl radical substituted by a morpholinyl group, a lower alkyl radical substituted by a piperidyl group, an ethylpiperidyl radical; a lower dialkylamino radical; a lower alkyl radical substituted by a pyridyle group, their acid addition salts with acids and their quaternary ammonium salts, the two R radicals being identical or different.

9. A process according to claim 7, in which the coupling and condensation agents are added in two successive steps.

10. A process according to claim 4, in which the nitrogen-containing compound is an amino acid selected from the group consisting of β-alanine, ε-aminocaproic acid, amino-acids having their carboxyl groups esterified by an N-hydroxylsuccinimide group, and amino-acids carrying both —SH groups and —$NH_2$ groups capable of forming a heterocycle in the presence of the —CHO groups of the organic compound to be bound onto said support.

11. A process according to claim 4, in which the nitrogen-containing compound is a hydrazine selected from the group consisting of p-hydrazino-benzoic acid, and adipic dihydrazide.

12. A process according to claims 1 or 4, in which the bound compound is a polyamine selected from the group consisting of spermidine, diaminopropylamine and spermine.

13. A process according to claim 1, in which the bound compound is an amino-acid selected from the group consisting of β-alanine, ε-amino-caproic acid, amino-acids having their carboxyl groups esterified by an N-hydroxylsuccinimide group, and amino-acids carrying both —SH groups and —$NH_2$ groups capable of forming a heterocycle in the presence of the —CHO group of the organic compound to be bound onto said support.

14. A process according to claims 1 or 4, in which the amino compound attached by covalent bonds to said insoluble solid support is, a basic dye.

15. A process according to claims 1, or 4, in which the covalent binding of the side chains on the support is effected in a non-agglutinant buffer, containing no free —NH$_2$ groups and at a pH betweenn 6.0 and 8.8.

16. A process according to claims 1, 4, 5, in which the covalent binding is followed by the desorption of remaining non-coupled reagents.

17. A process according to claims 1, 4 or 5, in which the insoluble solid support is selected from the group consisting of latex spheres, agarose beads, dextran beads, and activated glass beads.

18. A process according to claims 1, 4 or 5, in which the insoluble solid support to which are bound the said side chains, carries carboxyl groups, through the intermediary of which the side chains are bound on said support.

19. A process according to claims 1, 4 or 5, in which the solid insoluble support carries —NH$_2$ groups through the intermediary of which the said side chains are bound on said support.

20. A process for chemically binding according to claims 1, 4 or 5, wherein said oxidation of the —CH$_2$OH group to a —CHO group, is effected with sodium periodate.

21. A process according to claims 1, 4 or 5, in which the oxidation of the —CH$_2$OH group to a —CHO group is effected enzymically.

22. A process according to claim 21, in which the enzyme used to carry out the oxidation of the —CH$_2$OH group to a —CHO group enzymically is selected from the group consisting of glucose-oxidase, fucose-oxidase and galactose-oxidase, where the last-but-one residue of the carbohydrate chain is respectively glucose, fucose or galactose.

23. A process according to claim 1, 4 or 5, in which the organic compound containing a carbohydrate residue is subjected, prior to the transformation of at least one of the —CH$_2$OH groups thereof to a —CHO group by oxidation, to a treatment with neuraminidase, when the terminal residue of the carbohydrate chain is sialic acid, which treatment eliminates said sialic acid.

24. A process according to any one of claims 1, 4 or 5, in which the binding of the organic compound havig a carbohydrate residue is effected through the intermediary of said carbohydrate residue, by transforming two adjacent functional groups of said residue into —CHO functions, then causing these —CHO groups and reacting said groups with a reactive —NH$_2$ of the side chains bound to the insoluble solid support.

25. A process according to any one of claims 1, 4 or 5, in which the oxidation reaction of the carbohydrate residue of the organic compound to be bound to the support is effected at about pH 6.

26. The process of claim 1 further comprising using an oxidizing agent to aid in the oxidation.

27. A process according to claim 26, in which the excess of oxidising agent is eliminated at the end of the said oxidation reaction.

28. An immunochemical reagent for agglutinating a biologically active analyate comprising a support base having a size which permits agglutination and having a side chain with 3 to 20 carbon atoms and at least one reactive —NH$_2$ covalently bound to said support base; said side chain having attached thereto an organic compound being capable of agglutinating said analyte without reducing the biological activity of said analyte; said side chain selected from the group consisting of aromatic amines, polyamines having at least three amine groups, amino-acids aliphatic hydrazines bearing an acid group, aromatic hydrazines bearing an acid group, and a coupled compound formed by coupling a compound selected from the group consisting of amines, polyamines, diacids, amino-acids, aliphatic hydrazines bearing an acid group and aromatic hydrazines bearing an acid group, by the intermediary of the compound's reactive —NH$_2$, with a nitrogen-containing compound by carrying also at least one reactive —NH$_2$ and selected from the group consisting of aliphatic amines, aromatic amines, aliphatic hydrazines, aromatic hydrazines, and amino-acids; said support base selected from the group consisting of latex spheres, agarose beads, dextran beads, and activated glass beads.

29. A support according to claim 28, in which the side chains covalently bound onto said support result from the coupling of a compound selected from the group consisting of amines, polyamines, diacids, amino-acids, aliphatic and aromatic hydrazines bearing an acid group, by the intermediary of its reactive —NH$_2$, with a nitrogen-containing compound carrying at least one reactive —NH$_2$ and selected from the group consisting of aliphatic amines, aromatic amines, aliphatic hydrazines, aromatic hydrazines, and amino-acids.

30. A support according to claim 29, in which the insoluble solid support carries chains of hexamethylene-diamine (HMD) advantageously coupled through the intermediary of their reactive —NH$_2$ to adipic dihydrazide, or p-hydrazinobenzoic acid.

31. A support according to claim 29, in which the insoluble solid support carries a side chain selected from the group consisting of spermidine, diamino-propyla-mine, spermine, and amino-acids having its carboxyl group esterified by a N-hydroxyl-succinimide group, and coupled through the intermediary of their reactive —NH$_2$, to adipic dihydrazide, p-hydrazino or benzoic acid.

32. A support according to claim 29, in which the insoluble solid support carries side chains comprising an amino-acid selected from the group consisting of β-alanine and ε-amino-caproic acid coupled to diaminopropane, adipic dihydrazide, or p-hydrazino-benzoic acid.

33. A support according to claim 29, in which said side chains are amino-acids carrying both —SH and —NH$_2$ groups capable of forming a heterocycle in the presence of the —CHO group of the organic compound to be bound.

34. A support according to claim 33, in which the amino acid carrying both a —SH and a —NH$_2$ group, bound to said support, is cysteine or one of its homdogues, which forms in the presence of the —CHO group of the compound to be bound unto said support, a thiazolidine derivative.

35. A colored support according to claim 29, in which the side chains fixed to the support result from the coupling of an amine or polyamine with an acid function, and a basic dye selected from the group consisting of aliphatic amines, aromatic amines and hydrazines whereby the support is colored.

36. A support according to claim 35, further comprising a non-agglutinating buffer to preserve said support.

* * * * *